United States Patent [19]

Wiesmet

[11] Patent Number: 4,869,483
[45] Date of Patent: Sep. 26, 1989

[54] PATIENT SUPPORT APPARATUS

[75] Inventor: Eugen Wiesmet, Amberg, Fed. Rep. of Germany

[73] Assignee: Siemens Aktiengesellschat, Munich, Fed. Rep. of Germany

[21] Appl. No.: 201,023

[22] Filed: Jun. 1, 1988

[30] Foreign Application Priority Data

Jun. 12, 1987 [DE] Fed. Rep. of Germany ....... 8708335

[51] Int. Cl.$^4$ ............................................. A61G 13/00
[52] U.S. Cl. .................................................... 269/322
[58] Field of Search ............... 269/322, 323, 324, 325, 269/326, 901, 910, 242; 378/195, 196, 209; 108/138, 137, 102; 5/81 B, 81 C, 65, 90

[56] References Cited

U.S. PATENT DOCUMENTS

| | | |
|---|---|---|
| 1,823,534 | 9/1931 | Frutkow et al. . |
| 3,466,439 | 9/1969 | Setala .................... 269/322 |
| 3,550,759 | 12/1970 | Papen . |
| 3,652,851 | 3/1972 | Zaalberg ............... 269/322 |
| 3,751,028 | 8/1973 | Scheininger et al. ........ 269/322 |
| 4,131,802 | 12/1978 | Braden et al. ............ 269/322 |
| 4,520,800 | 6/1985 | Kowalski . |
| 4,575,064 | 3/1986 | Menor ................... 269/322 |
| 4,700,415 | 10/1987 | Di Matteo et al. ............. 5/81 C |
| 4,718,133 | 1/1988 | Di Matteo et al. ............. 5/81 B |
| 4,726,082 | 2/1988 | Di Matteo et al. ............. 5/81 B |
| 4,776,047 | 10/1988 | Di Matteo et al. ............. 5/81 C |

FOREIGN PATENT DOCUMENTS

| | | |
|---|---|---|
| 67681 | 4/1892 | Fed. Rep. of Germany . |
| 8515656.6 | 11/1986 | Fed. Rep. of Germany . |
| 131215 | 8/1919 | United Kingdom . |
| 1374999 | 11/1974 | United Kingdom . |

Primary Examiner—Robert C. Watson
Attorney, Agent, or Firm—Hill, Van Santen, Steadman & Simpson

[57] ABSTRACT

An apparatus for supporting a patient during medical treatment has a patient bearing plate having an opening therein in which a medical treatment device can be inserted. The opening is entirely or partially closeable by two slide elements moveable independently of each other toward and away from each other. Each slide element is wrapped by a continuous belt, and each belt is attached to one of two opposite edges which limit the opening in the bearing plate. As the slide element is moved, the continuous belt remains stationary, with the slide element moving within the loop formed by the belt.

3 Claims, 1 Drawing Sheet

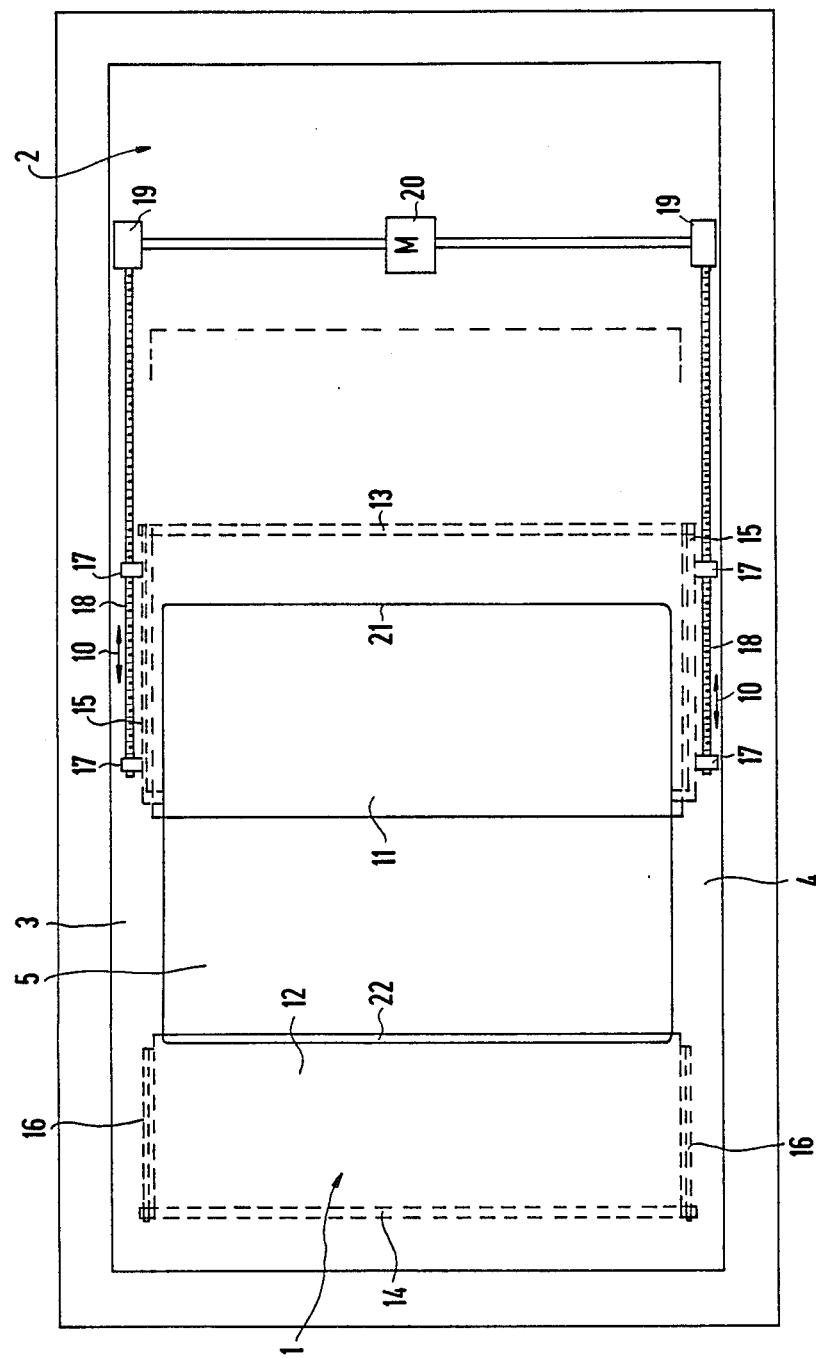

4,869,483

PATIENT SUPPORT APPARATUS

BACKGROUND OF THE INVENTION

1. Field of the Invention

The present invention is directed to a patient support apparatus of the type having a bearing plate provided with an opening for the application of a medical treatment device to a patient supported on the bearing plate.

2. Description of the Prior Art

Patient supports are used in medical treatment to support a patient while administering medical treatment to the patient by means of a therapy device insertable in an opening in the patient support. Such support devices are used, for example, in a lithotripsy work station wherein a shockwave generator is applied to the patient through the opening. It is known to provide a shockwave generator adjustable along three axes beneath the patient support apparatus, with the shockwave generator being capable of movement from a standby position through the opening to a treatment position. The opening must be relatively large to permit the shockwave generator to be applied to the desired area of the body surface of the patient. A large opening, however, is disadvantageous because the patient is not supported in the treatment region. It is conceivable to provide an opening no bigger than the size required to permit the shockwave generator to be applied to the patient through the opening, however, this would mean that it would be necessary to position the patient exactly on the bearing plate, so that the region of the body surface to which the shockwave generator is to be applied is precisely accessible through the opening. Such exact positioning of the patient, however, is burdensome for the operating personnel, and is uncomfortable for the patient and may even be painful for the patient under certain conditions, because considerable forces must be exerted on the patient.

SUMMARY OF THE INVENTION

It is an object of the present invention to provide a patient support table having an opening for applying a medical treatment device to a patient on the support apparatus wherein the patient is satisfactorily supported in the treatment region without requiring an exact positioning of the patient on the bearing plate relative to the opening.

The above object is achieved in accordance with the principles of the present invention in a patient support apparatus having a bearing plate with an opening therein which can be entirely or partially closed by two slide elements. The slide elements are adjustable toward and away from each other by means of respective continuous belts respectively wrapping the two slide elements. The opening in the bearing plate is defined on opposite sides by two edges, and each of these edges has one of the belts attached thereto so that the belt remains stationary while the respective slide element wrapped by the belt moves inside the belt.

When placing the patient on the bearing plate, it is thus sufficient to merely approximately position the patient with respect to the opening, because the opening itself, defined by the slide elements, can be displaced so that the region of the body surface of the patient to which the treatment device is to be applied is accessible. The size of the opening can also be selected by independently actuating movement of the slide elements, so that the opening has a size no bigger than is required for the application of the treatment device. A good support of the patient in the treatment region is thus insured.

A particular advantage of the patient support apparatus described herein is that the slides are moveable within the respective belts without relative motion between the belts and the patient. The slides can therefore be easily adjusted even with the patient resting thereon. It is also possible to completely close the opening when therapy with the treatment device is not to be undertaken, for example, if no shockwave treatment using a shockwave generator is to be undertaken, but only an x-ray exposure is to be prepared.

In a preferred embodiment, the slides contained within the belts are disposed beneath the bearing plate, and are each adjustable along the longitudinal axis of the patient support apparatus.

DESCRIPTION OF THE DRAWINGS

FIG. 2 is a plane view of the patient support apparatus constructed in accordance with the principles of the present invention shown in FIG. 1.

DESCRIPTION OF THE PREFERRED EMBODIMENTS

Figure 1:
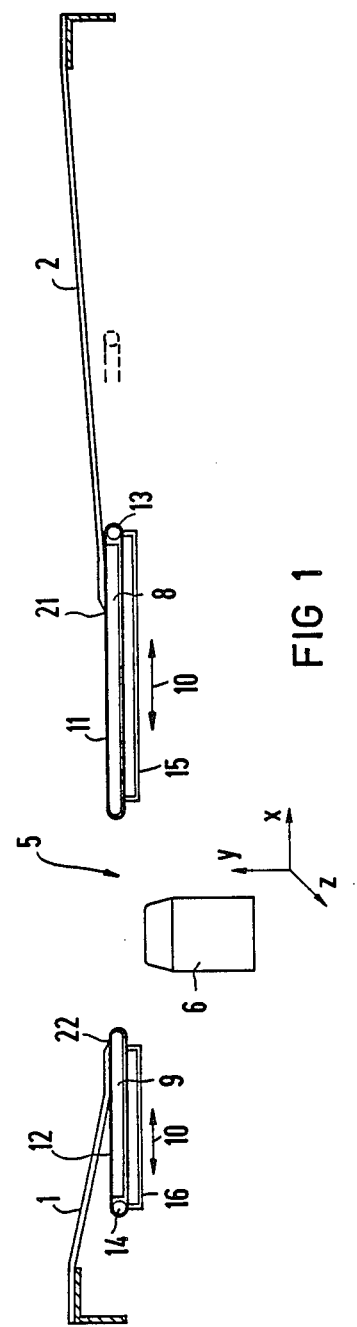
FIG. 1 a side view of a patient support apparatus constructed in accordance with the principles of the present invention.

As shown in FIG. 1, a patient support apparatus has a bearing plate including two sections 1 and 2, with the section 1 functioning as a shoulder rest for a patient. The support apparatus may be used, for example, to support a patient for kidney stone disintegration. The sections 1 and 2 are connected by side webs 3 and 4, with the sections 1 and 2 and the webs 3 and 4 defining and limiting an opening 5 through which a treatment device 6, such as a shockwave generator disposed beneath the support apparatus, can be applied to the patient. The treatment device 6 is adjustable along three axes, as indicated by the coordinate axis system shown in the drawing.

For partially or completely closing the opening 5, two slide elements 8 and 9 are disposed beneath the bearing plate. The slide elements 8 and 9 are adjustable independently of each other along the longitudinal direction of the bearing plate, as indicated by the two double arrows 10. The slide elements 8 and 9 are each wrapped by respective continuous belts 11 and 12. The belt 11, in addition to wrapping the slide element 8, is guided around a roller 13 at a side of the slide element 8 facing away from the opening 5, and the belt 12 similarly is guided around a roller 14 at a side of the slide element 9 facing away from the opening 5. The belts 11 and 12 are rigidly attached, for example by gluing, to respective edges 21 and 22 of the sections 1 and 2 of the bearing plate, which define opposite sides of the opening 5. When the slides 8 and 9 together with the respective rollers 13 and 14 are moved in the direction of the double arrows 10, no relative motion between the belts 11 and 12 and the bearing plate (or a patient lying thereon) occurs.

For adjusting the position of the slide elements 8 and 9, the elements 8 and 9 have respective clips 15 and 16 attached laterally thereto. The clips 15 and 16 are motor-adjustable in the direction of the double arrows 10. An exemplary embodiment for such motor displacement is shown in FIG. 2. In this embodiment, the clips 15 carry receptacles or rings 17 which are interiorly threaded, and which receive threaded spindles 18. The spindles 18 are rotated by an electric motor 20 by a suitable gearing arrangement 19. Upon rotation of the spindles 18, the slide element 8 moves in the direction of the double arrow 10 because the motor 20 and the gearing arrangements 19 are rigidly attached to the base of the patient support apparatus. The elements 18, 19 and 20, as the slide elements 8 and 9, are disposed beneath the bearing plate.

An identical adjustment means (not shown) is allocated to the slide element 9, which is actuatable independently of the above-described adjustment means for the slide element 8. It is thus possible to adjust the region of the opening 5 which is exposed by the slide elements 8 and 9 when they only partially close the opening 5. The opening can be adjusted both in position and size.

Other suitable adjustment means such as, for example, toothed racks may be used instead of the threaded spindles for adjusting the positions of the slide elements 8 and 9.

The right most final position of the slide element 8, together with the belt 11, in which it entirely exposes the opening 5, is shown in dashed lines in FIGS. 1 and 2. The slide element 9, together with the belt 12, are shown in their left most final position, and can be adjusted from this final position toward the right of the drawing. This slide element is shorter in longitudnal extent than the slide element 8, because a smaller adjustment distance is available at the corresponding end of the bearing plate at which the slide element 9 is disposed.

Although modifications and changes may be suggested by those skilled in the art it is the intention of the inventor to embody within the patent warranted hereon all changes and modifications as reasonably and properly come within the scope of his contribution to the art.

I claim as my invention:

1. A patient support apparatus comprising:
   a bearing plate for supporting a patient and having an opening therein with opposite edges;
   two slide elements moveable toward and away from each other and disposed for at least partially closing said opening;
   two continuous belts respectively wrapping said slide elements, each continuous belt being rigidly attached to one of said edges of said opening such that upon movement of a slide element within a continuous belt, said continuous belt remains stationary relative to said bearing plate; and
   means for moving said slide elements independently toward and away from each other.

2. A patient support apparatus as claimed in claim 1, wherein said bearing plate has a longitudinal axis, and wherein said slide elements are moveable along said longitudinal axis.

3. A patient support apparatus as claimed in claim 1, wherein said slide elements and said belts are disposed beneath said bearing plate.

* * * * *